United States Patent
McDevitt et al.

(10) Patent No.: US 6,527,794 B1
(45) Date of Patent: *Mar. 4, 2003

(54) SELF-LOCKING SUTURE ANCHOR

(75) Inventors: Dennis McDevitt, Upton, MA (US); Jeffrey Halbrecht, San Francisco, CA (US); Richard Caspari, Maidens, VA (US)

(73) Assignee: Ethicon, Inc., Somerville, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/371,411

(22) Filed: Aug. 10, 1999

(51) Int. Cl.$^7$ .............................................. A61B 17/04
(52) U.S. Cl. ........................................ 606/232; 606/1
(58) Field of Search ................. 606/104, 232, 606/72–75, 80

(56) References Cited

U.S. PATENT DOCUMENTS

| | | | |
|---|---|---|---|
| 3,036,482 A | 5/1962 | Kenworthy et al. | 81/52.35 |
| 3,566,739 A | 3/1971 | Lebar | 85/72 |
| 3,708,883 A | 1/1973 | Flander | 32/10 A |
| 3,842,824 A | 10/1974 | Neufeld | 128/92 BA |
| 4,013,071 A | 3/1977 | Rosenberg | 128/92 B |
| 4,091,806 A | 5/1978 | Aginsky | 128/92 BC |
| 4,140,111 A | 2/1979 | Morrill | 128/92 E |
| 4,408,938 A | 10/1983 | Maguire | 411/71 |
| 4,484,570 A | 11/1984 | Sutter | 128/92 D |
| 4,492,226 A | 1/1985 | Belykh et al. | 128/92 BC |
| 4,506,670 A | 3/1985 | Crossley | 128/334 R |
| 4,590,928 A | 5/1986 | Hunt et al. | 128/92 D |
| 4,632,100 A | 12/1986 | Somers et al. | 128/92 |
| 4,708,132 A | 11/1987 | Silvestrini | 128/92 YF |
| 4,741,330 A | 5/1988 | Hayhurst | 128/92 YF |

(List continued on next page.)

FOREIGN PATENT DOCUMENTS

| | | | |
|---|---|---|---|
| DE | 3406961 | 5/1985 | A61B/10/00 |
| EP | 0058744 | 9/1984 | A61F/1/03 |
| EP | 0241240 | 10/1987 | A61B/17/04 |
| EP | 0260970 | 3/1988 | A61F/2/08 |
| EP | 0124489 | 7/1988 | F16B/19/10 |
| EP | 0251583 | 7/1988 | A61B/17/58 |
| EP | 0270704 | 4/1989 | A61B/17/58 |
| EP | 0232049 | 3/1990 | A61F/2/08 |

(List continued on next page.)

Primary Examiner—Michael Peffley
Assistant Examiner—Pete J Vrettakos
(74) Attorney, Agent, or Firm—Nutter McClennen & Fish LLP

(57) ABSTRACT

A tissue anchor having a length of filament held so that an applied force greater than a threshold force will cause the filament to move longitudinally, while an applied force less than the threshold force will not move the filament, and methods of attaching soft tissue to bone using such an anchor.

23 Claims, 4 Drawing Sheets

U.S. PATENT DOCUMENTS

| | | | | |
|---|---|---|---|---|
| 4,778,468 A | 10/1988 | Hunt et al. | | 623/16 |
| 4,834,752 A | 5/1989 | Van Kampen | | 623/13 |
| 4,870,957 A | 10/1989 | Goble | | 128/92 YF |
| 4,871,289 A | 10/1989 | Choiniere | | 411/48 |
| 4,873,976 A | 10/1989 | Schreiber | | 128/334 R |
| 4,927,421 A | 5/1990 | Goble | | 606/73 |
| 4,940,467 A | 7/1990 | Tronzo | | 606/66 |
| 4,944,742 A | 7/1990 | Clemow et al. | | 606/59 |
| 4,988,351 A | 1/1991 | Paulos et al. | | 606/72 |
| 5,013,316 A | 5/1991 | Goble et al. | | 606/72 |
| 5,037,422 A | 8/1991 | Hayhurst et al. | | 606/72 |
| 5,046,513 A | 9/1991 | Gatturna et al. | | 128/898 |
| 5,084,050 A | 1/1992 | Draenert | | 606/77 |
| 5,116,337 A | 5/1992 | Johnson | | 606/73 |
| 5,141,373 A | 8/1992 | Kendall | | 411/43 |
| 5,141,520 A | 8/1992 | Goble et al. | | 606/232 |
| 5,152,763 A | 10/1992 | Johnson | | 606/86 |
| 5,154,189 A | 10/1992 | Oberlander | | 128/898 |
| 5,169,400 A | 12/1992 | Murling | | 606/73 |
| 5,176,682 A | 1/1993 | Chow | | 606/72 |
| 5,207,579 A | 5/1993 | Li | | 606/72 |
| 5,209,753 A | 5/1993 | Biedermann et al. | | 606/72 |
| 5,224,946 A | 7/1993 | Hayhurst et al. | | 606/72 |
| 5,236,445 A | 8/1993 | Hayhurst et al. | | 606/232 |
| 5,248,231 A | 9/1993 | Denham et al. | | 411/43 |
| 5,257,637 A | 11/1993 | Gazayerli | | 128/898 |
| 5,258,015 A | 11/1993 | Li et al. | | 606/232 |
| 5,268,001 A | 12/1993 | Nicholson et al. | | 606/72 |
| 5,269,783 A | 12/1993 | Sander | | 606/72 |
| 5,324,308 A | 6/1994 | Pierce | | 606/232 |
| 5,326,205 A | 7/1994 | Anspach, Jr. et al. | | 411/43 |
| 5,354,298 A | 10/1994 | Lee et al. | | 606/72 |
| 5,411,523 A | 5/1995 | Goble | | 606/232 |
| 5,417,712 A | 5/1995 | Whittaker et al. | | 606/232 |
| 5,423,860 A | 6/1995 | Lizardi et al. | | 606/232 |
| 5,458,601 A | 10/1995 | Young Jr. et al. | | 606/72 |
| 5,464,427 A | * 11/1995 | Curtis et al. | | 606/232 |
| 5,472,452 A | 12/1995 | Trott | | 606/232 |
| 5,480,403 A | 1/1996 | Lee et al. | | 606/72 |
| 5,486,197 A | 1/1996 | Le et al. | | 606/232 |
| 5,489,210 A | 2/1996 | Hanosh | | 433/173 |
| 5,496,326 A | 3/1996 | Johnson | | 606/88 |
| 5,501,683 A | 3/1996 | Trott | | 606/72 |
| 5,501,695 A | 3/1996 | Anspach et al. | | 606/232 |
| 5,522,845 A | 6/1996 | Wenstrom, Jr. | | 606/232 |
| 5,534,012 A | * 7/1996 | Bonutti | | 606/232 |
| 5,545,180 A | 8/1996 | Le et al. | | 606/232 |
| 5,569,306 A | 10/1996 | Thal | | 606/232 |
| 5,571,104 A | 11/1996 | Li | | 606/72 |
| 5,584,835 A | * 12/1996 | Greenfield | | 606/73 |
| 5,658,313 A | 8/1997 | Thal | | 606/232 |
| 5,665,112 A | 9/1997 | Thal | | 606/232 |
| 5,683,419 A | 11/1997 | Thal | | 606/232 |
| 5,702,397 A | 12/1997 | Goble et al. | | 606/72 |
| 5,702,462 A | 12/1997 | Oberlander | | 623/20 |
| 4,716,893 A | 1/1998 | Fischer et al. | | 128/92 YF |
| 5,709,708 A | 1/1998 | Thal | | 606/232 |
| 5,814,073 A | * 9/1998 | Bonutti | | 606/232 |
| 5,845,645 A | * 12/1998 | Bonutti | | 128/898 |
| 5,911,721 A | 6/1999 | Nicholson | | 606/72 |
| 5,935,129 A | 8/1999 | McDevitt et al. | | 606/72 |
| 5,935,134 A | * 8/1999 | Pedlick et al. | | 606/104 |
| 5,957,953 A | * 9/1999 | DiPoto et al. | | 606/232 |
| 5,980,558 A | * 11/1999 | Wiley | | 606/232 |
| 5,980,559 A | * 11/1999 | Bonutti | | 606/232 |
| 6,056,772 A | * 5/2000 | Bonutti | | 606/232 |
| 6,086,608 A | * 7/2000 | Ek et al. | | 606/232 |
| 6,123,711 A | * 9/2000 | Winters | | 606/73 |
| 6,267,766 B1 | * 7/2001 | Burkhart | | 606/72 |

FOREIGN PATENT DOCUMENTS

| | | | | |
|---|---|---|---|---|
| EP | 0340159 | 1/1993 | | A61B/17/58 |
| EP | 0409364 | 9/1994 | | A61B/17/04 |
| EP | 0574707 | 8/1997 | | A61B/17/04 |
| EP | 0611557 | 4/1999 | | A61F/2/08 |
| FR | 2054731 | 5/1971 | | A16J/13/00 |
| FR | 2346591 | 10/1977 | | F16B/13/06 |
| FR | 2622430 | 5/1989 | | A61B/17/58 |
| GB | 2084468 | 4/1982 | | A61F/1/00 |
| GB | 2248778 | 4/1992 | | A61F/2/08 |
| WO | 8809157 | 1/1988 | | A61F/5/04 |
| WO | 8901767 | 9/1989 | | A61F/5/04 |
| WO | 9204874 | 2/1992 | | A61B/17/56 |
| WO | 9502998 | 2/1995 | | A61B/17/04 |
| WO | 9515726 | 6/1995 | | A61B/17/56 |
| WO | 9529636 | 9/1995 | | A61B/17/00 |
| WO | 9838938 | 9/1998 | | A61B/17/68 |

* cited by examiner

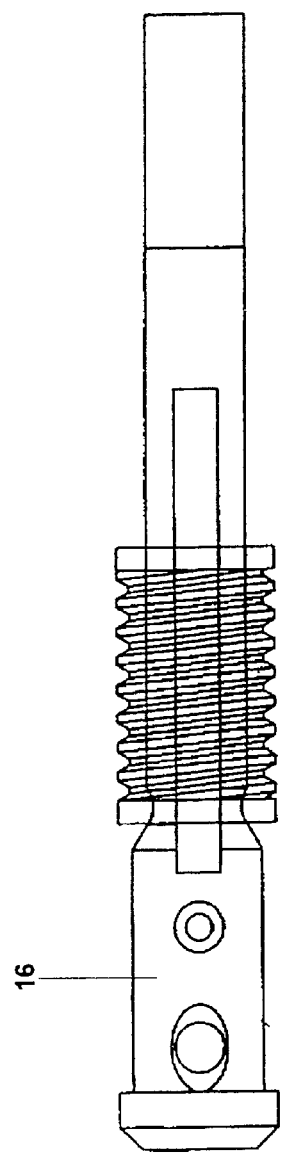
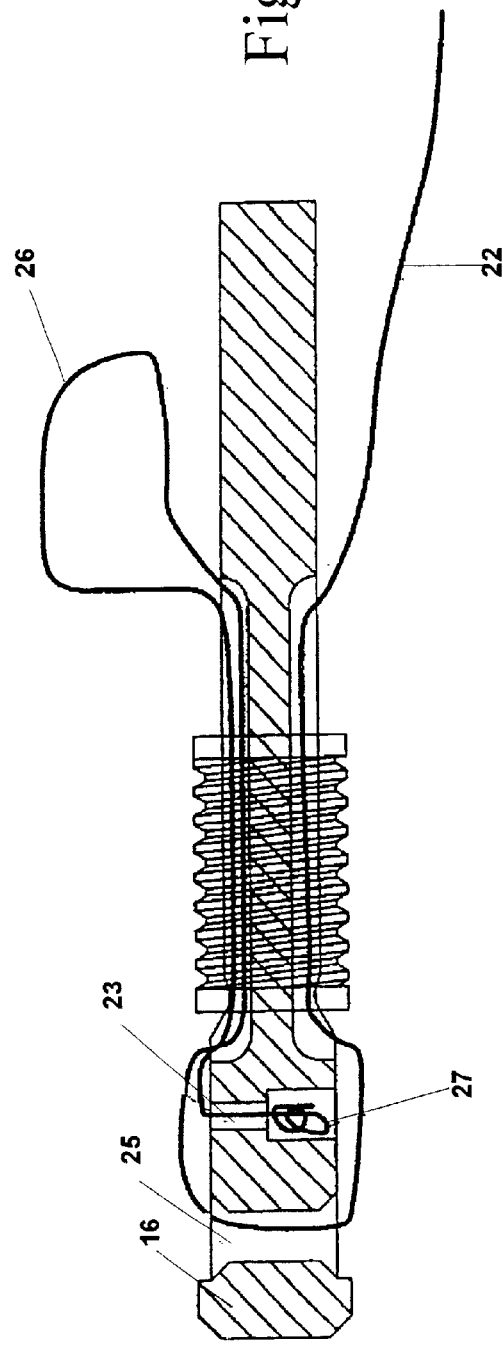
Figure 3(a)
Figure 3(b)

SELF-LOCKING SUTURE ANCHOR

BACKGROUND OF THE INVENTION

This invention relates to surgical fasteners, e.g., anchors that secure sutures to bone, a meniscus, or other tissue. It further relates to a suture anchor that attaches a suture to tissue without the use of knots, and to methods of securing tissue using one or more anchors and a length of suture.

Many surgical procedures require the attachment of soft tissue, e.g., ligament or tendon grafts, to bone. This is typically accomplished by anchoring a suture in bone, for example with a screw, pin, or other bone anchoring device, and looping the suture around or stitching the suture to the soft tissue. When this process is completed, the surgeon generally must knot the suture to secure the tissue. This knotting process can be difficult and tedious, particularly during laparoscopic or endoscopic procedures, where the surgeon must remotely manipulate the suture using tools inserted through an endoscopic tube. Further, as many as six knots are often required to secure one suture. These knots may "stand proud" above the tissue and interfere with movement and healing.

One advance which has been proposed is the anchor apparatus disclosed by Goble, et al., in U.S. Pat. No. 5,702,397. That apparatus comprises an anchor body through which a suture passes, and which contains a clamping mechanism such as a spherical element within the anchor body. When the suture is pulled in a proximal direction, the clamp is urged into contact with the anchor body, thereby holding the suture in place. When the suture is pulled in a distal direction, the clamp disengages, and the suture can move freely through the anchor body. At least one end of the suture is stitched and/or knotted to soft tissue.

Several knotless suture anchor assemblies have recently been proposed by Thal in U.S. Pat. Nos. 5,569,306; 5,658,313; 5,665,112; and 5,683,419. These describe suture anchors which secure a filament having a small loop at one end. In some embodiments, another length of suture ends in a small block, which is passed through the loop to secure the tissue. While these structures can be secured without knots, the block used to secure the suture may itself stand proud above the tissue, causing discomfort and interfering with healing. In other embodiments, the anchor itself is passed through the small loop, creating a larger loop which is used to hold tissue.

U.S. Pat. No. 5,709,708, also by Thal, describes a suture anchor utilizing a continuous loop of suture material, which secures the tissue in a similar manner. As in the other Thal knotless anchors, the tension of the suture is dependent on the length of specially provided suture, which cannot be adjusted. Thus, these anchors cannot be used in surgical operations in which it is necessary to tighten a loop of suture to secure soft tissue.

The tying of suture knots presents difficulties in other surgical procedures, as well. For example, tears occur commonly in the menisci of athletes. The simplest method of repairing such a tear is to stitch it closed by passing a length of suture through the tissue and tying. However, the needles used in such surgery are very difficult to manipulate during endoscopic surgery, and the knots used to secure the suture may interfere with healing as described above. These difficulties are particularly severe in the restricted space of the joint capsule of the knee, a common location for such injuries. Other devices such as darts and clamps have also been proposed for this purpose; see for example U.S. Pat. Nos. 5,154,189; 5,269,783; and 5,702,462. Like suture knots, these devices may cause considerable discomfort during healing of the tear. Further, if made of non-bioabsorbable materials, a second surgery must be performed to remove the devices from the meniscus after healing.

A need thus exists for an improved technique and apparatus for securing tissues without the use of knots. A further need exists for such techniques and apparatus which also permit the position of the suture to be readily adjusted. A still further need exists for such apparatus which is small enough to avoid discomfort, which is amenable to fabrication from bioabsorbable materials, and which can be used either in bone or in soft tissue.

SUMMARY OF THE INVENTION

The above needs are among those met by the invention, which provides an anchoring device that can be embedded in bone or soft tissue, that permits suture length and/or tension to be readily adjusted, and that can be secured without the use of knots.

In one aspect of the invention, a suture anchor suitable to be embedded in bone has a cavity which holds a filament (e.g., a suture) by interference fit. The anchor holds the suture tightly enough to resist "operational" forces to which the suture is subjected subsequent to deployment, e.g., during movement of the bones and/or soft tissues to which the suture is attached. However, the interference fit is weak enough to allow the suture to be pulled longitudinally through the cavity by a stronger force.

In use, such an anchor can be placed with some slack in the suture. The suture can then be tightened by pulling on one of its ends (with the larger force). It is an advantage of the invention that the tightening of the suture can be reversed, simply by pulling on a loop formed by the suture or by pulling on its opposite end. The suture does not loosen in normal use, however, since the forces required to move during deployment are greater than those exerted by the bones and/or tissues to which it is attached.

In a related aspect, the anchor may hold the suture at two points, forming a loop. The loop can be disposed around tissue and, then, tightened by pulling one end of the suture, thereby securing the tissue. Again, if the loop is drawn too tight, it can be loosened by pulling firmly.

The invention also provides methods for attaching soft tissue to bone. In these methods, an anchor of the type described above can be emplaced in bone. The soft tissue is secured by stitching or by catching a portion of the tissue in a loop of suture, which is subsequently tightened. The suture can be tightened or loosened as necessary during deployment, and need not be knotted.

These and other aspects of the invention are evident in the drawings and in the description that follows.

BRIEF DESCRIPTION OF THE DRAWING

The invention is best understood with reference to the drawings, in which:

FIG. 3 is an illustration of a suture anchor according to the invention before deployment.

DETAILED DESCRIPTION OF PREFERRED EMBODIMENTS

Figure 1A:
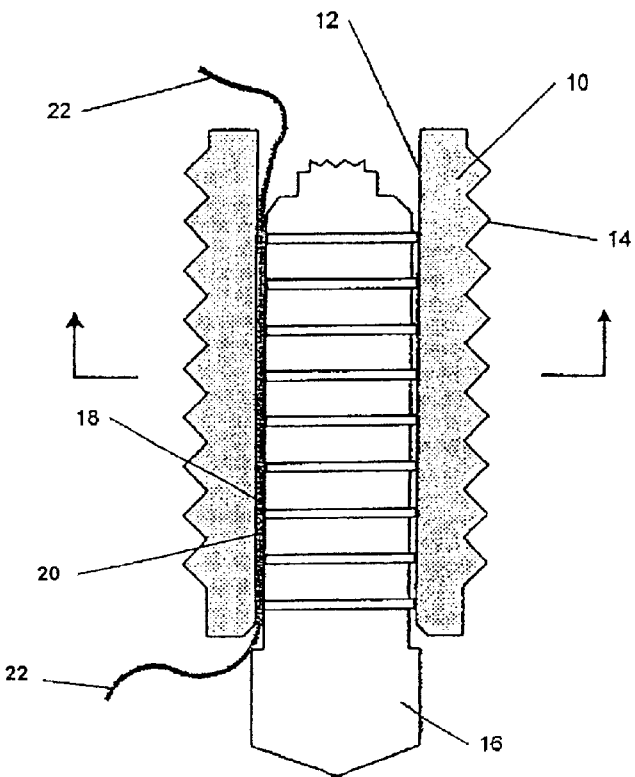
FIGS. 1 and 2 are illustrations of suture anchors according to the invention, adapted to be embedded in bone.

FIG. 1a shows a cutaway view of a suture anchor according to the invention. The anchor comprises an anchoring element 10, which is adapted to be embedded in a bone tunnel or in soft tissue, and comprises an axial channel 12. In the embodiment shown, element 10 comprises a series of ridges 14 on its outer surface, which aid in securing the element, for example, in a bone tunnel. It will be understood that the ridges 14 are not a necessary element of the anchor, and may be omitted if desired. The anchor 10 further comprises an insertion stem 16. When the anchor is in the deployed position shown in FIG. 1a, the insertion stem 16 is held within the axial channel 12, e.g., by interference fit. In preferred embodiments, the insertion stem 16 is slightly larger than the axial channel 12, so that the stem 16 forces the anchoring element 10 to expand when it is inserted therein, thereby securing the anchor firmly in the bone tunnel.

Figure 1B:
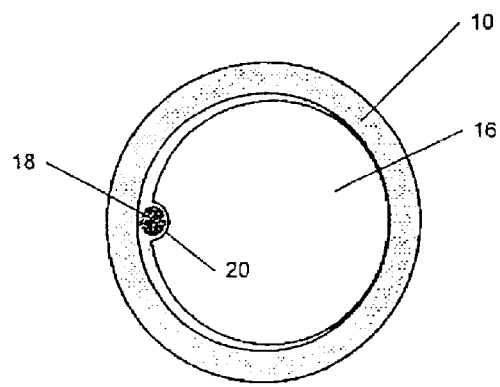

The anchor further comprises a filament 18, e.g., a suture, disposed between the anchoring element 10 and the insertion stem 16. In the preferred embodiment shown in FIG. 1a and 1b, the insertion element comprises a suture channel 20. This channel guides the suture 18, and holds it in compression against the anchoring element 10. The configuration of anchoring element 10, insertion stem 16, and suture 18 can be seen clearly in FIG. 1b, which shows a cross-sectional view of the anchor at the point indicated by the arrows of FIG. 1a. The mild compression of the suture 18 in the channel 20 provides a frictional resistance to prevent movement of the suture when tension is applied to one of its free ends 22. This frictional resistance is overcome when a tension greater than the threshold tension is applied to a free end of the suture. The suture 18 may then slide longitudinally through the channel 20, allowing the length of the free ends 22 to be adjusted.

It will be understood that the configuration of suture 18 in FIG. 1 represents only one of many possible embodiments of the invention. In particular, it will often be preferable to pass the suture between the insertion stem 16 and the anchoring element 10 multiple times, for example, in order to form a loop segment. In other embodiments of the invention, the compression of the suture may be stronger, so that the threshold tension which would be necessary to move the suture is close to or exceeds the breaking strength of the suture. In such embodiments, the length of the free ends is no longer adjustable once the compression on the suture is applied.

Figure 2A:
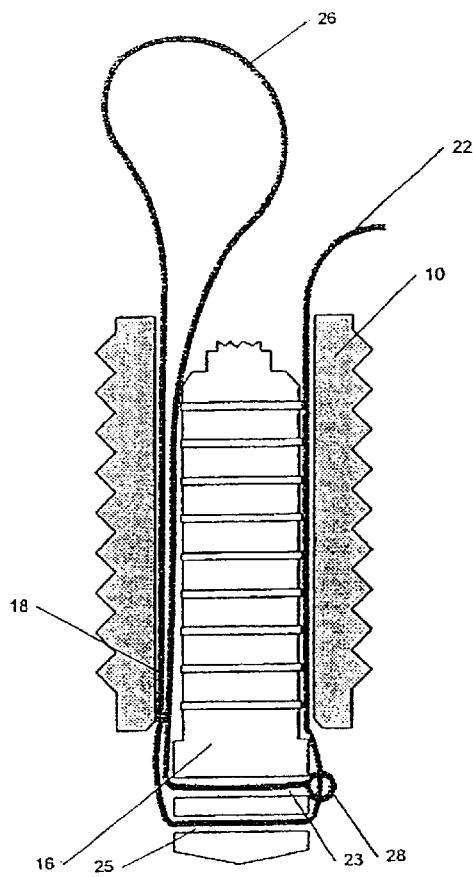
Figure 2B:
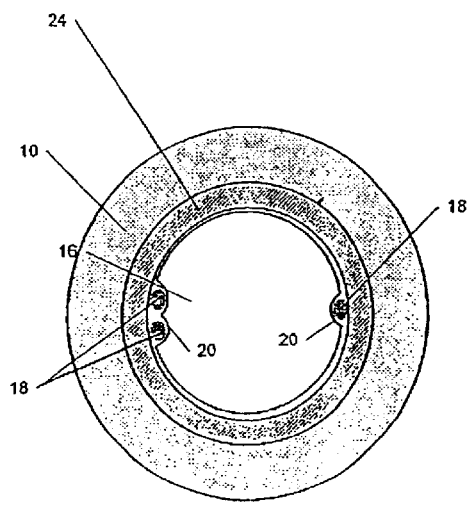

In one such embodiment, the suture (or other filament) may be formed with a small loop at one end, which is used to secure the suture to the anchor. This embodiment is illustrated in FIGS. 2a and 2b; the former depicting a cross-section of the anchor along the axis of symmetry; and the latter depicting a transverse section. The head of suture 18 comprises a small loop 28; e.g., disposed at the distal end of the anchor. The suture passes between the insertion stem 16 and the anchoring element 10, forms a loop segment 26, and passes back between the insertion stem and the anchoring element. The suture then passes through head loop 28, back up between the insertion stem 16 and the anchoring element 10, and ends in free end 22. The loop segment 26 can be tightened by pulling free end 22, and loosened by pulling the loop segment 26 itself. Because of the mechanical advantage afforded by looping of the suture, the force required to loosen the suture by pulling on loop 26 is twice the force required to tighten the suture by pulling on free end 22. In the embodiment shown, the suture passes through two channels 23, 25 in the anchor 16; one of these channels 25 could be eliminated so that the suture would pass around the head of the anchor.

FIGS. 3a and 3b illustrate a different embodiment of the anchor, in which the suture is secured by a small knot 27 rather than a loop. FIG. 3a is a plan view of the anchor, and FIG. 3b is a longitudinal cross-section.

Figure 4A:
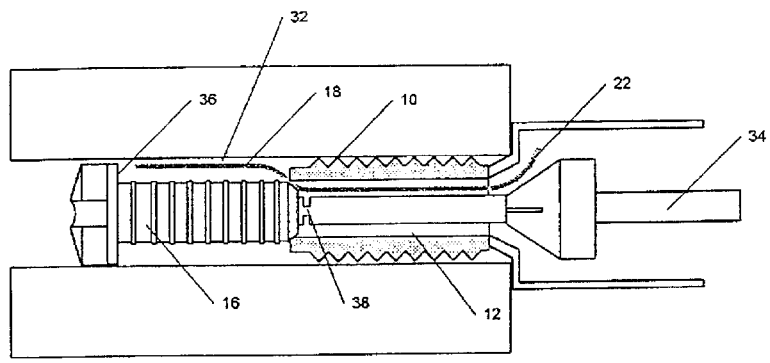
FIGS. 4A–4C illustrate a deployment process for teh anchors shown in FIGS. 1 and 2.
Figure 4B:
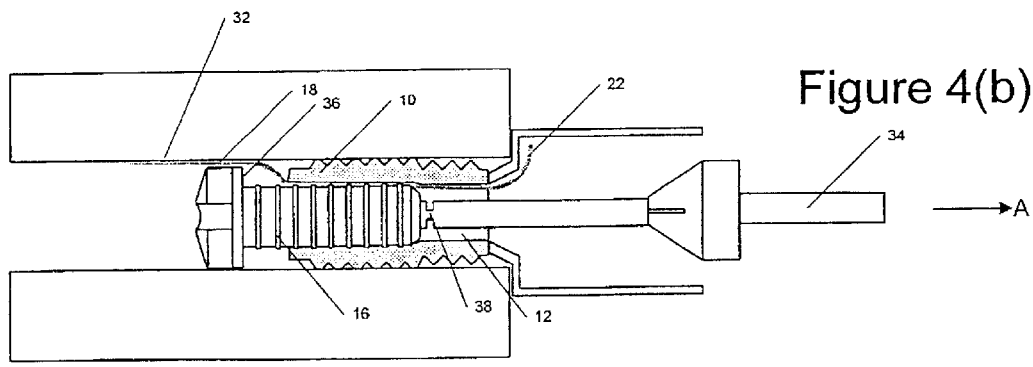
Figure 4C:
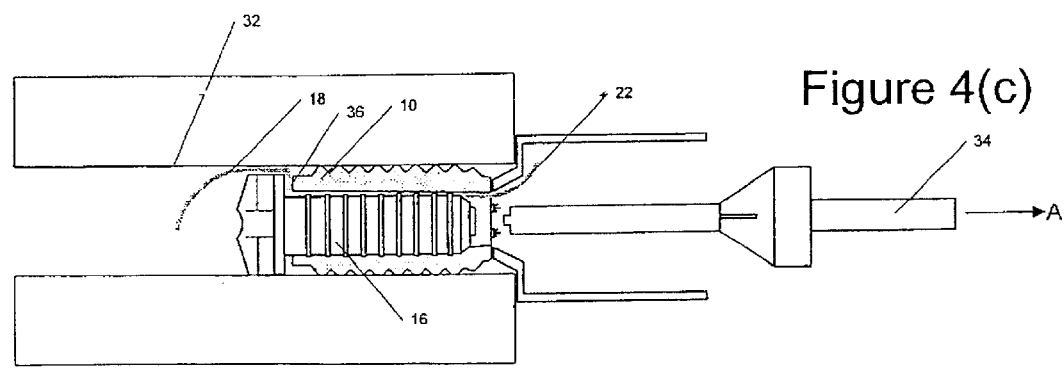

FIGS. 4a–4c illustrate a deployment process for the anchors shown in FIGS. 1 and 2. Only a portion of the suture is shown in FIGS. 4a–4c; preferably, the suture will be looped in the fashion shown in FIG. 2 or FIG. 3. FIG. 4a shows an anchor placed in bone tunnel 32, connected to deployment apparatus 34. FIG. 4b illustrates the insertion element 16 being pulled into the axial channel 12 of anchoring element 10. Tension is applied to the stem of insertion element 16 (in the direction shown by arrow A) by the colleted stem-pulling portion of the deployment device 34, while the anchoring element 10 is held substantially immobile within bone hole by the anchor-holding portion of that device. These forces act to move the insertion element 16 in the direction of arrow A such that larger diametered portion of insertion element is pulled into the axial channel 12 of anchoring element 10. As a result, the wall of the anchoring element 10 expands outwardly and into the walls of the bone hole 32. As shown in FIG. 4c, the insertion stem is pulled proximally through the axial bore 12, until further motion is retained by abutment of flange 36 with the distal end of anchoring element 10. At this point, the deployment device continues to exert tension on the stem 16, causing frangible portion 38 to shear. This facilitates removal of the excess portion of the stem 16 and, likewise, disengages the deployment device 34. The suture 18 can be adjusted by pulling firmly on free end 22.

The suture anchors of the invention can be provided in a variety of sizes and materials, depending on the intended application. For example, a typical anchor intended to be embedded in the shoulder blade, for use in repair of the rotator cuff of an adult, might have a length in the range of 8–15 mm and a diameter in the range of 3–6 mm. Such an anchor might be capable, for example, of holding a #2 suture with a threshold force in the range of 25–35 lbs. (As it is used herein, the term "threshold force" describes a pulling force above which a filament moves longitudinally through an anchor, and below which the filament substantially does not move through the anchor). It is generally desirable for the anchor to consist of biocompatible material, e.g., implant grade high density polyethylene, low density polyethylene (PE 6010 and PE 2030), polypropylene (13R9A and 23M2: all made by Rexene, Dallas, Tex.) or surgical implant grade steel. In some embodiments, the anchor may comprise a bioabsorbable material, e.g., poly-1-lactide or a lactide-glycolide composition.

In an exemplary embodiment of the methods of the invention, the anchor illustrated in FIGS. 3a and 3b can be used to repair a torn rotator cuff by reattachment of the rotator cuff to the scapula. An anchor such as that illustrated in FIG. 3a, which holds a loop of suture by interference fit, is embedded in a tunnel drilled, for example, in the scapula. The loop of suture and the free end of the suture extend out from the scapula at the proximal end of the anchor.

When the anchor is disposed in the bone tunnel, a portion of the torn rotator cuff is passed through the suture loop. The loop is then tightened by pulling with a force greater than the threshold force on the free end of the suture. This tightens the loop, drawing the tissue against the anchor and securing it to the bone without knotting the suture. The free end of the suture may then be trimmed, if desired.

The invention may be used with various anchor designs, depending on the nature of the surgical repair. In particular, designs similar to those described in copending U.S. application Ser. No. 08/813,914, e.g., at FIG. 5 and in the accompanying text, and in copending U.S. application Ser. No. 08/814,149, and in the accompanying text, both of which are incorporated herein by reference, may be adapted to hold a suture in accordance with the teachings herein.

Other embodiments of the invention will be apparent to those skilled in the art from a consideration of the specification or practice of the invention disclosed herein. For example, while the invention has been described primarily in the contexts of securing soft tissue to bone and of repairing tears in soft tissue, it may also be used to secure or repair cartilage, ligaments, or other tissues. It is intended that the specification and examples be considered as exemplary only, with the true scope and spirit of the invention being indicated by the following claims.

What is claimed is:

1. A device for anchoring a filament to tissue or bone, comprising:

an anchor member adapted to be embedded in bone, the anchor having a cavity therein; and a filament having a first and a second portion extending from the cavity, the filament being held in the cavity by interference fit, the filament substantially not moving in response to a tensional force less than a threshold force applied to any of the first mad second portion, the filament moving longitudinally in response to a tensional force greater than the threshold force applied to any of the first and second portion, wherein the filament has a breaking tension greater than the threshold force.

2. The device of claim 1, wherein the threshold force is in a range 25–35 pounds.

3. A device for anchoring a filament to tissue or bone, comprising:

an anchor member adapted to be embedded in bone, the anchor having a cavity therein, wherein the anchor member comprises, an anchoring element for insertion into a hole in tissue, the anchoring element including an axial channel extending between proximal and distal ends thereof, the anchoring element being slidably mounted on an insertion stem, the insertion stem including a portion having a greater outer diameter than an inner diameter of the axial channel, that portion being referred to herein as the portion of the greater diameter, the insertion stem being adapted to move proximally in the axial channel to cause the portion of greater diameter to move at least partially through that channel and, thereby, to cause the anchoring element to expand to a pressure fit with the bone hole; and a filament having a first and second portion extending from the cavity, the filament being held in the cavity by interference fit, the filament substantially not moving in response to a tensional force less than a threshold force applied to any of the first and second portion, the threshold force being less an the breaking tension of the filament, the filament moving longitudinally in response to a tensional force greater than the threshold force applied to any of the first and second portion.

4. The device of claim 3, where the cavity is formed by and disposed between a surface of the anchoring element and a surface of the insertion stem.

5. The device of claim 1, wherein at least two sections of the filament, disposed between the first and second portions, pass through the anchor member, so that a loop segment is defined between the sections.

6. The device of claim 5, wherein the loop segment can be tightened by pulling any of the first and second portions of filament with a tension greater than the threshold tension.

7. The device of claim 5, wherein the loop segment can be loosened by pulling the loop segment with a tension greater than twice the threshold tension.

8. The device of claim 1, wherein the anchor member is adapted to be embedded in a tunnel in bone.

9. The device of claim 1, wherein the anchor member comprises a biocompatible material selected from the group consisting of polyethylene, polypropylene, steel, poly-l-lactide and lactide-gylicolide compositions.

10. A device for anchoring soft tissue to bone, comprising:

an anchor member adapted to be embedded in a bone tunnel and having a cavity therein; and a filament having a first and a second portion extending from the cavity, the filament being held in the cavity by interference fit, the filament substantially not moving in response to a tensional force less than a threshold force applied to any of the first and second portion, the filament moving longitudinally in response to a tensional force greater than the threshold force applied to any of the first and second portion, whereby the filament can be used to secure soft tissue, wherein the filament has a breaking tension greater than the threshold force.

11. The device of claim 10 wherein the threshold force is in a range 25–35 pounds.

12. A device for anchoring soft tissue to bone, comprising:

an anchor member adapted to be embedded in a bone tunnel and having a cavity therein, wherein the anchor member comprises, an anchoring element for insertion into a hole in tissue, the anchoring element including an axial channel extending between proximal and distal ends thereof, the anchoring element being slidably mounted on an insertion stem, the insertion stem including a portion having greater outer diameter than an inner diameter of the axial channel, that portion being referred to herein as the portion of greater diameter, the insertion stem being adapted to move proximally in the axial channel to cause the portion of greater diameter to move at least partially through that channel and, thereby, to cause the anchoring element to expand into a pressure fit with the bone hole; and a filament having a first and second portion extending from the cavity, the filament being held in the cavity by interference fit, the filament substantially not moving in response to a tensional force less than a threshold force applied to any of the first and second portion, the filament moving longitudinally in response to a tensional force greater than the threshold force applied to any of the first and second portion, whereby the filament can be used to secure soft tissue.

13. The device of claim 12, where the cavity is formed by and disposed between a surface of the anchoring element and a surface of the insertion stem.

14. The device of claim 10, wherein at least two sections of the filament, disposed between the fist and second portions, pass through the anchor member, so that a loop segment is defined between the sections.

15. The device of claim 14, wherein the loop segment can be tightened by pulling any of the first and second portions of filament with a tension greater than the threshold tension.

16. The device of claim 15, wherein the soft tissue can be secured by passing it through the loop segment, and then tightening the loop segment.

17. The device of claim 14, wherein the loop segment can be loosened by pulling the loop segment with a tension greater than twice the threshold tension.

18. The device of claim 10, wherein the anchor member comprises a biocompatible material selected from the group consisting of polyethylene, polypropylene, steel, poly-l-lactide and lactide-glycolide compositions.

19. A method of anchoring soft tissue to bone, comprising:

embedding an anchor member in a bone tunnel, the anchor member comprising a cavity, a filament having a first and a second portion extending from the cavity, the filament being held in the cavity by interference fit, the filament substantially not moving in response to a tensional force less than a threshold force applied to any of the first and second portion, the filament moving longitudinally in response to a tensional force greater than the threshold force applied to any of the first and second portion; and using the filament to attach soft tissue to the bone, wherein the filament has a breaking tension greater than the threshold tension.

20. The method of claim 19, wherein using the filament to attach soft tissue to the bone comprises:

passing a portion of the filament through at least one aperture in the soft tissue; and tightening the filament by applying a force greater than the threshold force to one portion of the filament, thereby causing it to move longitudinally.

21. The method of claim 19, wherein the threshold tension is in a range 25–35 pounds.

22. The method of claim 19, wherein the soft tissue is selected from the group consisting of a tendon, a ligament, a meniscus, and artificial soft tissue.

23. A method of anchoring soft tissue to bone, comprising:

embedding an anchor member in a bone tunnel, the anchor member comprising a cavity, wherein the anchor member comprises, an anchoring element for insertion into a hole in tissue, the anchoring element including an axial channel extending between proximal and distal ends thereof, the anchoring element being slidably mounted on an insertion stem, the insertion stern including a portion having a greater outer diameter than an inner diameter of the axial channel, that portion being referred to herein as the portion of greater diameter, the insertion stem being adapted to move proximally in the axial channel to cause the portion of greater diameter to move at least partially through that channel and, thereby, to cause the anchoring element to expand into a pressure fit with the bone hole;

a filament having a first and second portion extending from the cavity, the filament being held in the cavity by interference fit, the filament substantially not moving in response to a tensional force less than a threshold force applied to any of the first and second portion, the threshold force being less than the breaking tension of the filament, the filament moving longitudinally in response to a tensional force greater than the threshold force applied to any of the first and second portion; and using the filament to attach soft tissue to bone.

* * * * *

UNITED STATES PATENT AND TRADEMARK OFFICE
CERTIFICATE OF CORRECTION

PATENT NO. : 6,527,794 B1 Page 1 of 1
DATED : March 4, 2003
INVENTOR(S) : Dennis McDevitt, Jeffrey Halbrecht and Richard Caspari It is certified that error appears in the above-identified patent and that said Letters Patent is hereby corrected as shown below:

<u>Column 5,</u>
Line 25, "mad" should be -- and --

<u>Column 6,</u>
Line 65, "fist" should be -- first --

Signed and Sealed this

Eighth Day of July, 2003

JAMES E. ROGAN
*Director of the United States Patent and Trademark Office*